United States Patent
Motoi et al.

(10) Patent No.: US 7,615,764 B2
(45) Date of Patent: *Nov. 10, 2009

(54) INFORMATION ACQUISITION APPARATUS, CROSS SECTION EVALUATING APPARATUS, CROSS SECTION EVALUATING METHOD, AND CROSS SECTION WORKING APPARATUS

(75) Inventors: Taiko Motoi, Kanagawa (JP); Rie Ueno, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 79 days.

This patent is subject to a terminal disclaimer.

(21) Appl. No.: 11/410,901

(22) Filed: Apr. 26, 2006

(65) Prior Publication Data

US 2006/0197017 A1    Sep. 7, 2006

Related U.S. Application Data

(60) Division of application No. 10/826,350, filed on Apr. 19, 2004, now Pat. No. 7,053,370, which is a continuation-in-part of application No. 10/488,974, filed as application No. PCT/JP02/10277 on Oct. 2, 2002, now abandoned.

(30) Foreign Application Priority Data

Oct. 5, 2001 (JP) ............................ 2001-310032
Nov. 19, 2003 (JP) ............................ 2003-389358

(51) Int. Cl.
*G21K 7/00* (2006.01)
*G01N 23/00* (2006.01)

(52) U.S. Cl. ............... 250/492.3; 250/309; 250/492.21; 250/306; 250/370; 257/429

(58) Field of Classification Search ............... 250/306, 250/309, 310, 443.1, 492.1, 492.2, 492.21, 250/492.3
See application file for complete search history.

(56) References Cited

U.S. PATENT DOCUMENTS 3,978,686 A   9/1976 Lechner et al.
5,244,820 A * 9/1993 Kamata et al. .............. 438/514

(Continued)

FOREIGN PATENT DOCUMENTS

JP          58-005505          1/1983

(Continued)

OTHER PUBLICATIONS

O.M.N.D. Teodoro, et al.: "multitechnique surface analysis system: apparatus description" Vacuum, vol. 46, No. 8-10, 1995, pp. 1205-1209, XP002435142, p. 1208.

*Primary Examiner*—David A Vanore
*Assistant Examiner*—Michael Maskell
(74) *Attorney, Agent, or Firm*—Fitzpatrick, Cella, Harper & Scinto

(57) ABSTRACT

The invention provides a cross section evaluating apparatus capable of analyzing the cross sectional structure in a state where the temperature of the specimen is regulated. There is disclosed an information acquisition apparatus comprising a stage for placing the specimen, temperature regulation means for regulating the temperature of the specimen, exposure means for exposing a surface, of which information is desired, of the specimen, and information acquisition means for acquiring information relating to the surface exposed by the exposure means.

2 Claims, 13 Drawing Sheets

U.S. PATENT DOCUMENTS

| | | | |
|---|---|---|---|
| 5,440,122 A | 8/1995 | Yasutake | 250/443.1 |
| 5,473,165 A * | 12/1995 | Stinnett et al. | 250/492.21 |
| 5,753,924 A | 5/1998 | Swann | |
| 6,114,695 A | 9/2000 | Todokoro et al. | 250/310 |
| 6,300,630 B1 | 10/2001 | Veneklasen | 250/310 |
| 6,538,254 B1 * | 3/2003 | Tomimatsu et al. | 250/442.11 |
| 7,053,370 B2 * | 5/2006 | Motoi et al. | 250/306 |
| 2003/0066749 A1 * | 4/2003 | Golovchenko et al. | 204/192.32 |
| 2004/0262515 A1 | 12/2004 | Motoi et al. | 250/306 |

FOREIGN PATENT DOCUMENTS

| | | |
|---|---|---|
| JP | 1-181529 | 7/1989 |
| JP | 05-28946 | 2/1993 |
| JP | 7-312196 | 11/1995 |
| JP | 9-082261 | 3/1997 |
| JP | 9-82261 | 3/1997 |
| JP | 9-274883 | 10/1997 |
| JP | 9-306405 | 11/1997 |
| JP | 10-111223 | 4/1998 |
| JP | 11-260307 | 9/1999 |
| JP | 2000-114207 | 4/2000 |
| JP | 2000-149884 | 5/2000 |
| JP | 2000-162102 | 6/2000 |
| JP | 2000-215837 | 8/2000 |
| JP | 2000-513135 | 10/2000 |
| JP | 2001-84951 | 3/2001 |
| JP | 2003-194746 | 7/2003 |
| WO | 03/032360 | 4/2003 |

* cited by examiner

FIG. 1
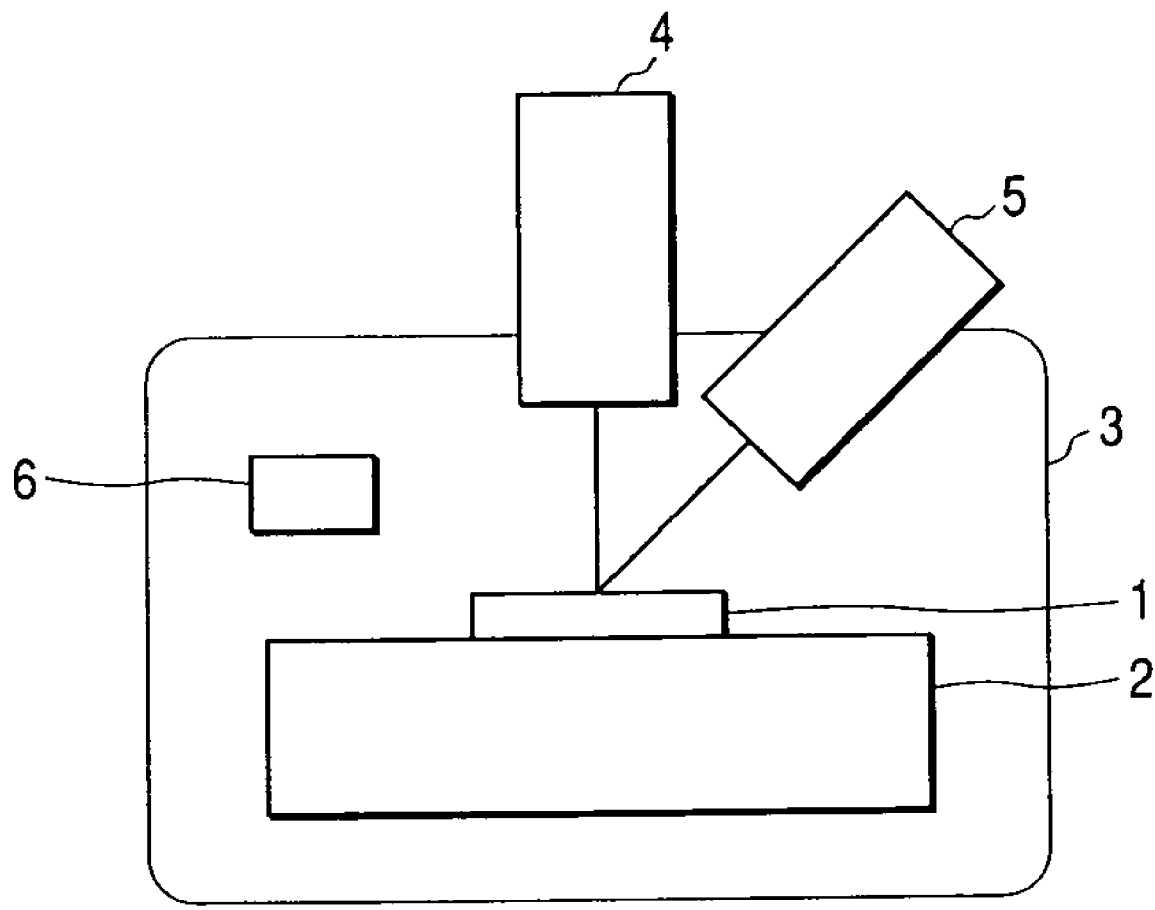
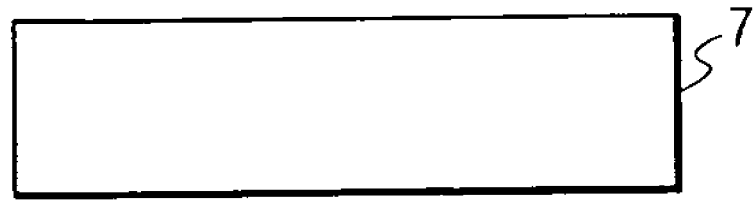

FIG. 2
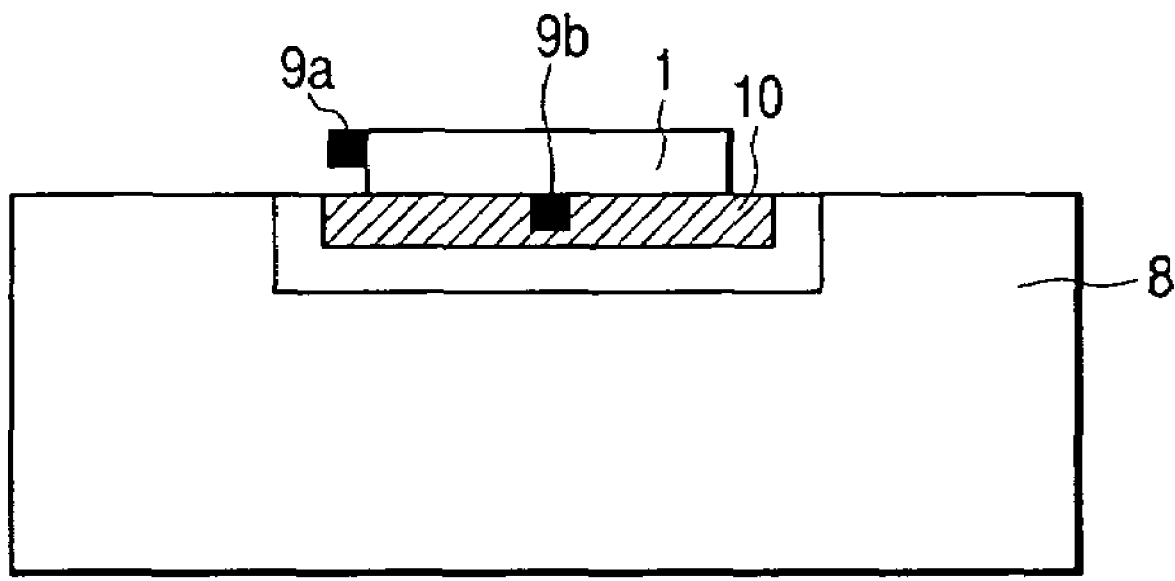
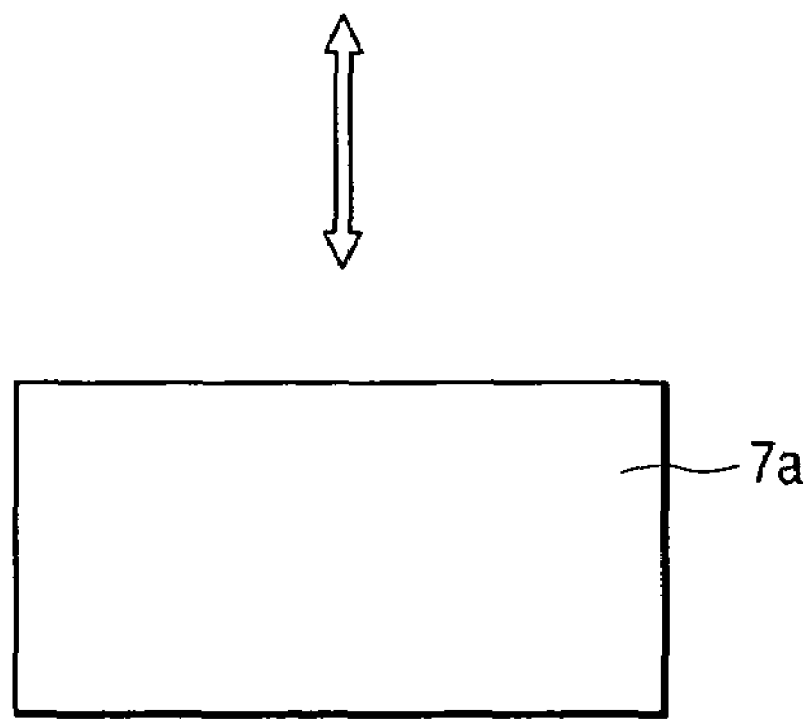

FIG. 5
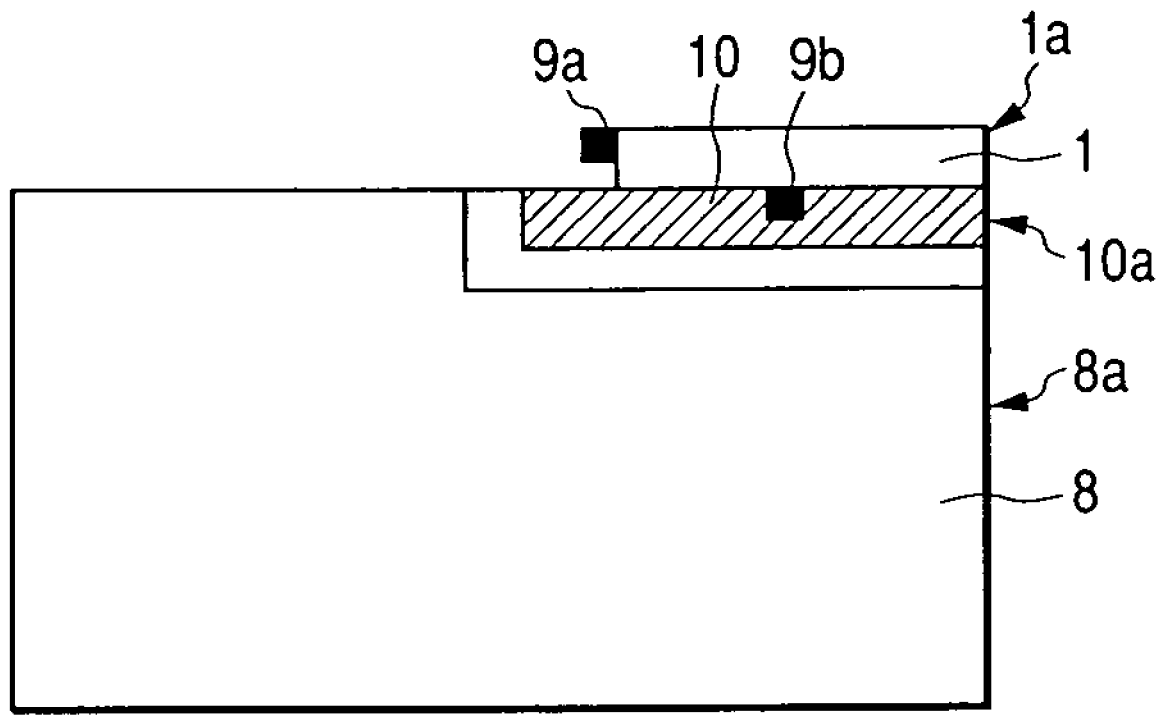
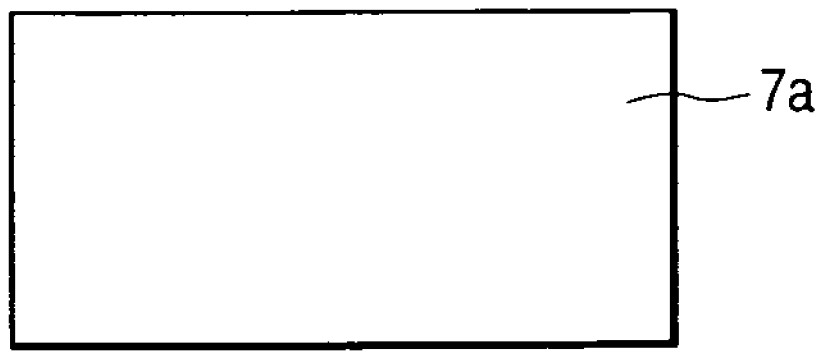

FIG. 7
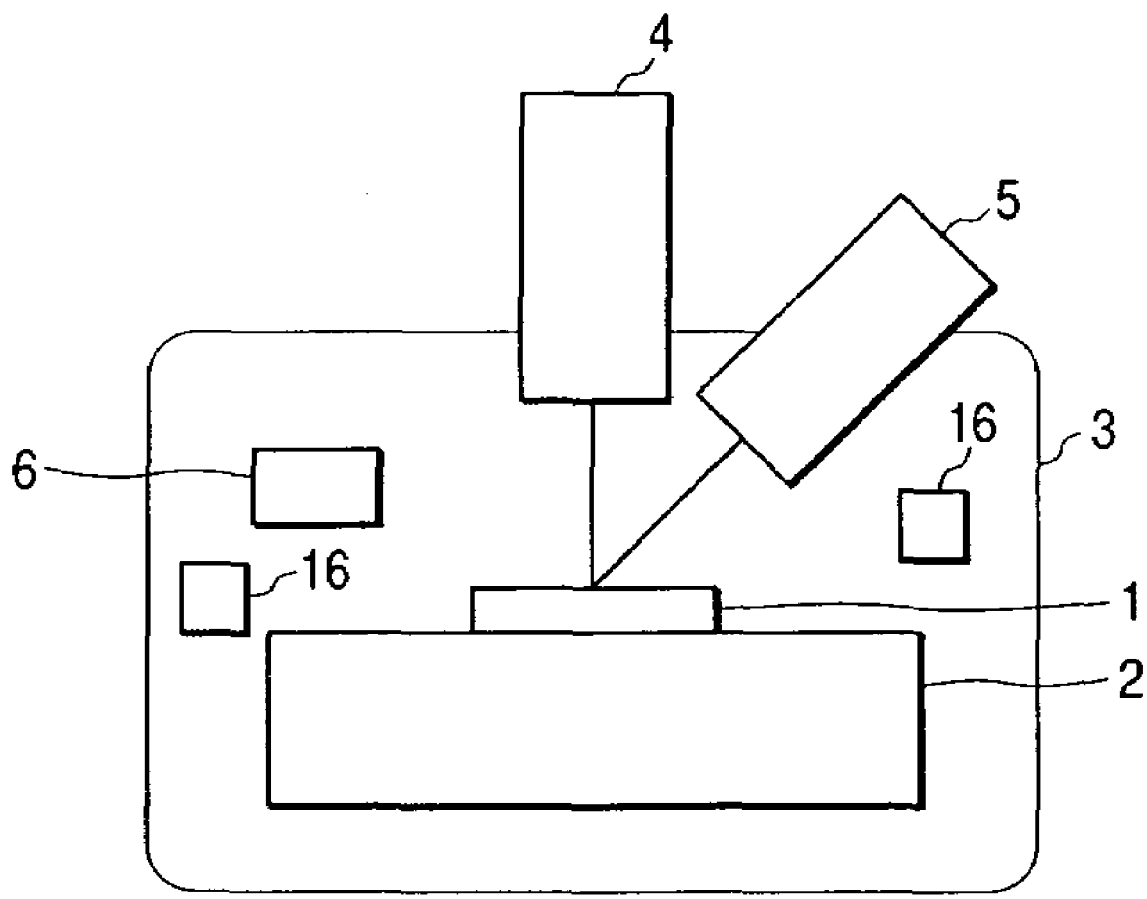
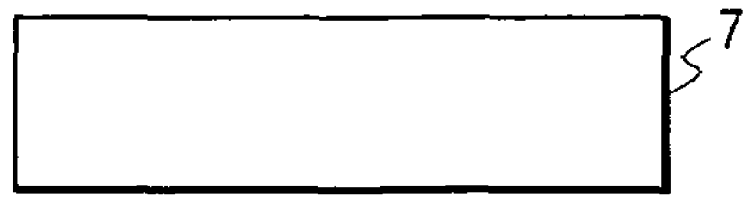

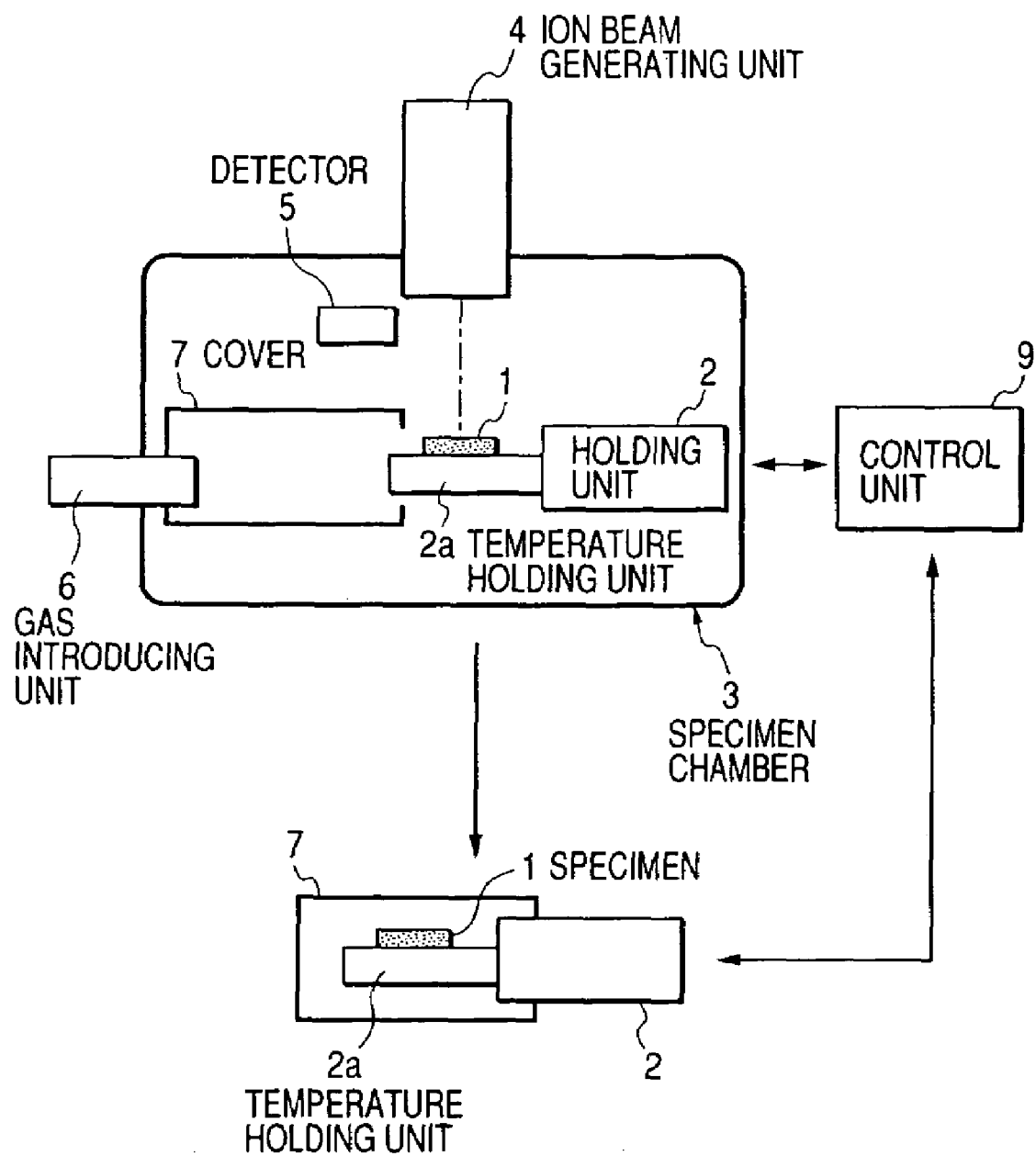

INFORMATION ACQUISITION APPARATUS, CROSS SECTION EVALUATING APPARATUS, CROSS SECTION EVALUATING METHOD, AND CROSS SECTION WORKING APPARATUS

This application is a divisional of application Ser. No. 10/826,350 filed Apr. 19, 2004, now allowed, which is a continuation-in-part of U.S. patent application Ser. No. 10/488,974, filed Mar. 9, 2004, the contents both of which are incorporated by reference herein.

This application is a continuation-in-part of application Ser. No. 10/488,974 filed on Mar. 9, 2004, which is the National Stage of International Application No. PCT/JP02/10277, filed on Oct. 2, 2002.

BACKGROUND OF THE INVENTION

1. Field of the Invention

The present invention relates to an information acquisition apparatus for acquiring information on a specimen, and more particularly to a cross section evaluating apparatus and a cross section evaluating method for evaluating the cross section of a specimen of which state and shape vary according to a change in temperature and a cross section working apparatus.

2. Related Background Art

The demand for evaluation of a cross section or formation of a fine structure in organic materials, including bio-origin materials and plastics, is increasing together with the recent increase of functional devices.

As the principal methods of preparing a cross section, utilized for obtaining information on the structure of an organic material, there are known, for example, a cutting method with a blade, an embedding method in resin, an embedding method by freezing, a breaking method by freezing, an ion etching method etc., but, in case of observing the internal structure of an organic material with an optical microscope, there is usually adopted a method of embedding the organic material in a resin and cutting it with a microtome.

However, the observation with the optical microscope is limited to a macroscopic analysis of the cross section, and, since the cut-out position cannot be designated, a large amount of work has been necessary in repeating the cross-section preparing operation, in order to achieve observation and analysis of the structure of the designated position.

For this reason, there has recently been developed an FIB-SEM apparatus in which a working function by an FIB (focused ion beam) apparatus is attached to an SEM (scanning electron microscope). The FIB apparatus irradiates a working specimen with a finely focused ion beam from an ion source, thereby achieving a working operation such as etching. The etching technology with such FIB apparatus is becoming more and more popular, and is currently widely employed for a structural analysis and a defect analysis of a semiconductor material or the like, and for preparing a specimen for a transmission electron microscope. The FIB-SEM apparatus is capable of executing a step of etching a specimen and a step of observing the cross section of the specimen by the SEM within a single apparatus, thus being capable of designating a cut-out position and observing and analyzing the structure in such designated position.

Such FIB-SEM apparatus has been proposed in various configurations. For example, the Japanese Patent Application Laid-Open No. H01-181529 proposes an apparatus capable, while the specimen is fixed, of SEM observation of the working depth in the course of FIB working and SIM (scanning ion microscope) observation of the surface of the specimen in the course of working. This apparatus is so constructed that a focused ion beam (FIB) from an FIB generation unit and an electron beam from an electron beam generation unit irradiates, with respectively different angles, a same position of the fixed specimen, and the working by the FIB and the SEM (or SIM) observation by detecting secondary electrons emitted from the specimen in response to the irradiation with the electron beam (or FIB) are alternately executed, whereby the working state of the specimen can be monitored in the course of the working process.

In addition, the Japanese Patent Application Laid-Open No. H09-274883 proposes a configuration of irradiating an electrode with a beam to prevent charging of the specimen in the course of FIB working, thereby enabling a highly precise working.

DISCLOSURE OF THE INVENTION

However, in case the aforementioned conventional FIB-SEM apparatus is used for observation and analysis of the cross-sectional structure of a specimen of which state or shape changes by the temperature such as an organic material, the heat generated in the course of FIB working causes a change in the temperature of the specimen, thereby varying the state or shape thereof, whereby the cross-sectional structure of the specimen cannot be exactly analyzed.

In consideration of the foregoing, an object of the present invention is to provide an information acquisition apparatus capable of resolving the aforementioned drawbacks and acquiring the information on the surface of which information is desired, in a state where the temperature of the specimen is regulated.

Another object of the present invention is to provide a cross section evaluating apparatus and a cross section evaluating method capable of resolving the aforementioned drawbacks and analyzing the cross section in a state where the temperature of the specimen is regulated.

Still another object of the present invention is to provide a working apparatus, a work portion evaluating apparatus and a working method, capable of resolving the aforementioned drawbacks, and of working a specimen and exactly acquiring the information of the work portion in a state where the temperature of the specimen is regulated.

The above-mentioned objects can be attained, according to the present invention, by an information acquisition apparatus comprising a stage for placing a specimen, a temperature regulation means for regulating the temperature of the specimen, an exposure means for exposing a surface of the specimen of which surface information is desired, and an information acquisition means for acquiring the information relating to the surface exposed by the exposure means.

According to the present invention, there is also provided a cross section evaluating apparatus comprising a stage for placing a specimen, a temperature regulation means for regulating the temperature of the specimen, an ion beam generation means for irradiating the specimen with an ion beam thereby cutting out a cross section or working the specimen, an electron beam generation means for irradiating the specimen with an electron beam, and a detection means for detecting an emission signal emitted from the specimen in response to the irradiation with the ion beam or the irradiation with the electron beam, to acquire information from the detection means is acquired.

There is also provided a cross section evaluating apparatus provided with the aforementioned cross section evaluating apparatus further comprising an information acquisition means for irradiating a predetermined portion of the specimen with the ion beam to cut out a cross section or work the specimen, scanning the surface of the predetermined portion or the cut-out cross section with the ion beam or the electron beam, and acquiring an image information relating to the surface of the predetermined portion or the cut-out cross section based on emission signals from plural point detected by the detection means in synchronization with the scanning.

According to the present invention, there is also provided a cross section evaluating method comprising the steps of regulating the temperature of a specimen, irradiating a predetermined portion of the specimen with an ion beam to cut out a cross section, and scanning the cut-out cross section with an electron beam and acquiring an image relating to the cross section from an emission signal emitted from plural points in synchronization with the scanning.

According to the present invention as described in the foregoing, the specimen is always subjected to temperature regulation, so that the specimen is always maintained at a desired temperature even in the course of FIB working and is therefore prevented from changes in the state or shape as encountered in the conventional technologies.

Also according to the present invention, the cross section working apparatus is provided, which is an apparatus for working the cross section of the specimen, comprising:

a stage for placing the specimen;

a temperature regulation means for regulating the temperature of the specimen;

a beam generation means for irradiating the specimen with a beam to execute a working of the specimen; and a sealing means for sealingly accommodating the specimen and the stage before conveying the stage and the specimen prior to processing.

In the present invention, with the specimen put into a state of a predetermined regulated temperature by the temperature regulation means, it is possible to execute a specimen working by the beam generating means, an acquisition of the information by the detection means, and a gas introduction into the interior of a cover fitted with gas introducing means after the cover fitted with atmospheric protection means is mounted.

Also according to the present invention, the temperature regulation means can be constituted by comprising cooling means which cools the specimen to temperatures below the room temperature.

Also according to the present invention, the stage, the beam generating means, and detection means are arranged in a chamber capable of controlling the atmosphere, and can be constituted by further comprising trap means for trapping the remaining gas in the interior of the chamber.

Also according to the present invention, a cross section evaluating method is provided, which is characterized by comprising:

a first step of regulating the temperature of the specimen;

a second step of irradiating a beam onto the specimen and cutting out the cross section thereof;

a third step of sealing the specimen which is temperature-regulated;

a fourth step of conveying the sealed specimen to another apparatus; and a fifth step of evaluating the conveyed specimen by another apparatus.

In the present invention, it is possible also to execute a step of introducing a gas around the specimen to be sealed.

Also in the present invention, the introduction gas may be a gas such as an inactive gas or a dry nitrogen gas which does not give any damage to the specimen.

In the present invention, a cross section not only indicates a plane inside the specimen seen from a point, but also, even in case the specimen is subjected to a working (including deposition or etching), a plane observable seen from a view point after such working.

Also according to the present invention, even in a specimen showing a change in the state or shape by a temperature change, the exposure of a surface of which information is desired and the acquisition of information are executed in a state where the temperature of such specimen is regulated, so that exact information can be acquired from the surface of which information is desired.

Also in case the present invention is applied to a cross section evaluating apparatus, there can be executed a working of the cross section, an observation (SEM or SIM observation) and an elementary analysis can be executed while a specimen, showing a change in the state or shape by a temperature change, is maintained at a desired temperature, so that there can achieved an exact morphological analysis of a micro cross section of the specimen can be executed.

BRIEF DESCRIPTION OF THE DRAWINGS

FIG. 1 is a view schematically showing the configuration of a scanning electron microscope for cross sectional observation, constituting a first embodiment of the cross section evaluating apparatus of the present invention;

FIG. 2 is a block diagram schematically showing the configuration of a specimen stage with a temperature controller, constituting an example of a temperature holding unit shown in FIG. 1;

FIG. 5 is a block diagram schematically showing the configuration of a specimen stage with a temperature controller, constituting an example of a temperature holding unit shown in FIG. 4;

FIG. 7 is a view schematically showing the configuration of a scanning electron microscope for cross sectional observation, constituting a fourth embodiment of the cross section evaluating apparatus of the present invention;

FIG. 8A is a schematic view showing an example of a cross section prepared by an FIB working, while

FIG. 9A is a schematic view showing an example of a cross section prepared by an FIB working, while

FIG. 10 is a schematic block diagram of a focused ion beam apparatus for cross section working, which is a sixth embodiment of the cross section evaluation apparatus of the present invention;

DESCRIPTION OF THE PREFERRED EMBODIMENTS

Figure 3:
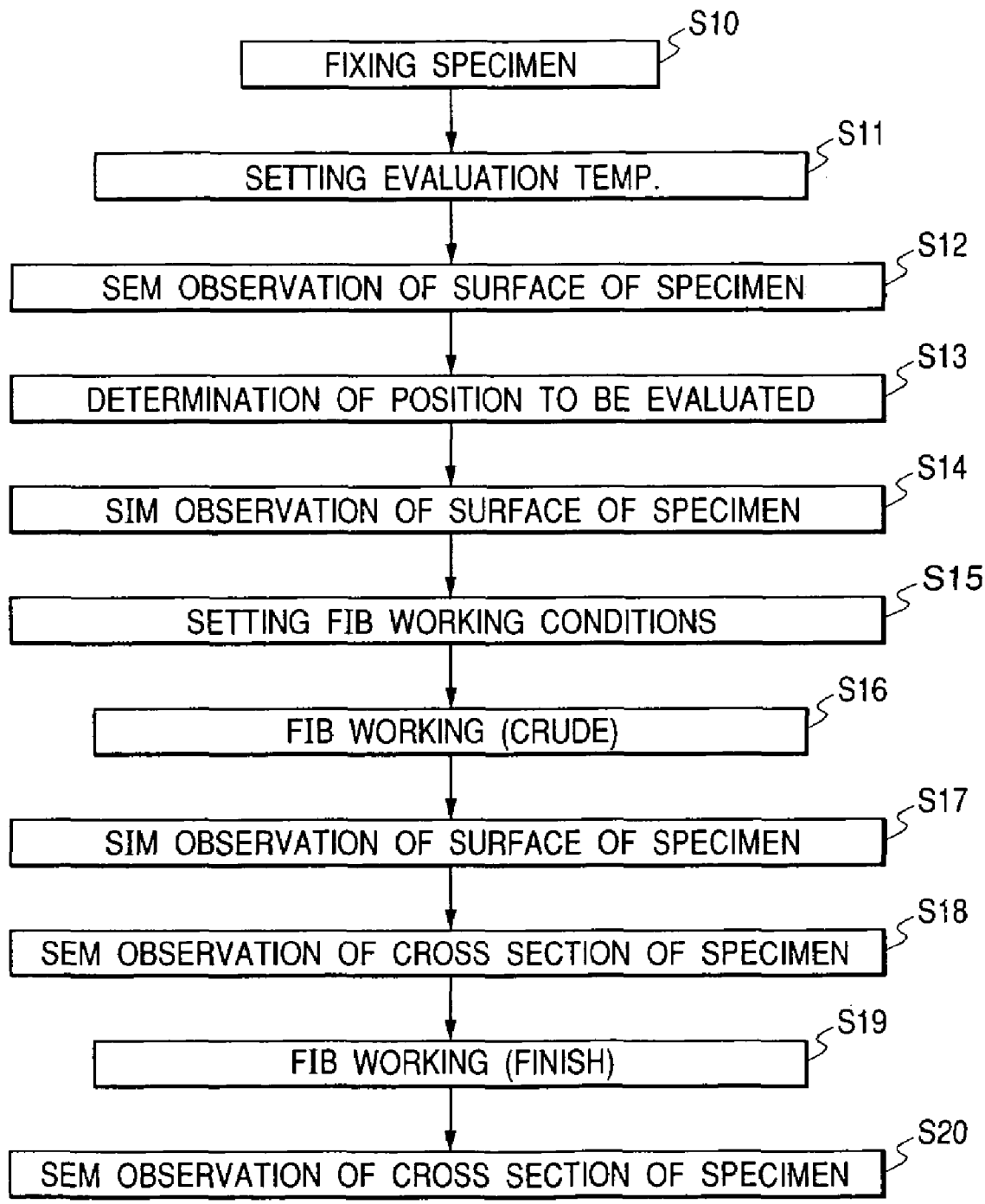
FIG. 3 is a flow chart showing a procedure of cross sectional evaluation, utilizing the scanning electron microscope for cross sectional observation shown in FIG. 1.

Now the present invention will be clarified in detail by embodiments thereof, with reference to the accompanying drawings.

Embodiment 1

FIG. 1 schematically shows the configuration of a scanning electron microscope for cross sectional observation, constituting a first embodiment of the cross section evaluating apparatus of the present invention. The electron microscope is provided with a temperature holding unit 2, on which a specimen 1 is fixed and which maintains the temperature of the specimen at a preset temperature. Temperature holding unit 2 can be accommodated in a specimen chamber 3.

Specimen chamber 3 is provided with an ion beam generation unit 4 for irradiating specimen 1, fixed to temperature holding unit 2 with an ion beam, and an electron beam generation unit 5 for irradiating the specimen with an electron beam and also with an electron detector 6 for detecting secondary electrons emitted from specimen 1 by the irradiation with the electron beam or the ion beam. The interior of specimen chamber 3 can be evacuated by a pump unrepresented in the figure to hold a predetermined low pressure, whereby the irradiation with the ion beam or the electron beam is rendered possible. In the present invention, the interior of the specimen chamber is preferably maintained at a pressure of $1 \times 10$ Pa to $1 \times 10^{-2}$ Pa.

Ion beam generation unit 4 is used for irradiating specimen 1 with the ion beam thereby cutting out a cross section, and it can also be used for SIM observation. In case of SIM observation, secondary electrons generated when specimen 1 is irradiated with the ion beam are detected by electron detector 6, and an image is formed based on a detection signal from electron detector 6.

Electron beam generation unit 5 is used for SEM observation. In case of SEM observation, the secondary electrons generated when specimen 1 is irradiated with the electron beam are detected by electron detector 6, and an image is formed based on a detection signal from electron detector 6.

The detection signal from electron detector 6 is supplied to a control unit 7, which executes image formations in the aforementioned SIM and SEM observations. For example, control unit 7 acquires image information (mapping information) from the detection signal supplied from electron detector 6, and forms an image by causing an unrepresented display apparatus to display such image information. In addition, control unit 7 controls the ion beam generation in ion beam generation unit 4 and the electron beam generation in electron beam generation unit 5, and controls the irradiation and scanning of the ion beam and the electron beam onto specimen 1. The beam scanning operation can be controlled in the beam side and/or in the stage side on which the specimen is fixed, but the control at the beam side is preferable in consideration of the scanning speed etc. Also the irradiating positions of the ion beam and the electron beam can be respectively so controlled that they mutually coincide on specimen 1.

The electron beam generation unit and the ion beam generation unit may be so constructed as disclosed in Japanese Patent Application Laid-Open Nos. H11-260307 and H01-181529.

(Configuration of Temperature Regulating Means)

Temperature regulating means in the present embodiment is provided with a temperature holding unit capable of regulating temperature of the specimen.

Temperature holding unit 2 is, for example, comprised of a specimen stage having a temperature controller. FIG. 2 schematically shows the configuration of the specimen stage with temperature controller.

Referring to FIG. 2, the specimen stage with temperature controller is comprised of a specimen stage 8 having a temperature varying mechanism 10 in a portion where specimen 1 is fixed, a thermometer 9a for directly detecting the temperature of specimen 1, a thermometer 9b mounting in a part of temperature varying mechanism 10 for detecting the temperature in the vicinity of specimen 1, and a temperature control unit 7a for regulating the temperature of temperature varying mechanism 10 based on the temperature detected by thermometer 9b to keep the temperature of specimen 1 at a preset temperature.

Though not represented in FIG. 2, there is also provided a display unit for displaying the temperature detected by thermometer 9a, whereby the operator can confirm the temperature of specimen 1, based on the temperature displayed on the display unit. Temperature control unit 7a may also be so constructed as to regulate the temperature in temperature varying mechanism 10 based on the temperatures detected by both the thermometers 9a and 9b, thereby controlling the temperature of specimen 1 in more precise manner.

Temperature varying mechanism 10 is constructed as a unit together with thermometer 9b, whereby a unit capable of control in a required temperature range can be installed in specimen stage 8. Such unit can be, for example, a high temperature unit having a heating mechanism such as a heater, or a low temperature having a cooling mechanism. Also, if necessary, there may be used a unit provided with a temperature varying function relating to both a lower temperature region than the room temperature and a higher temperature than the room temperature region of the room temperature.

Specimen stage 8 is capable of mechanically move specimen 1 in the vertical or horizontal direction, or rotate or incline specimen 1, thereby shifting specimen 1 to a desired position of evaluation. The movement control of specimen 1 by specimen stage 8 is conducted by the aforementioned control unit 7.

The aforementioned cooling mechanism can be comprised of a set of for example a Peltier element or a helium freezing device. Otherwise there may be adopted a system of providing a coolant pipe for flowing a cooling medium in a side of the temperature holding unit opposed to the specimen fixing portion to maintain a cooling medium such as liquid nitrogen and water in thermal contact with the temperature holding unit.

Also in order to increase the absorption efficiency for the heat generated in the course of working; there is preferably adopted a measure for improving the contact efficiency between the specimen and the cooling unit (temperature holding unit).

Such measure can be, for example, the use of a specimen holder which is so constructed as to wrap around the specimen but not to intercept the optical system of the apparatus to be used in the working and observing operations, or working the specimen in a shape matching the shape of the stage and supporting the specimen with a maximum contact area on the stage.

It is also possible to provide a cooling member which covers only a non-worked area of the specimen so as not to intercept the beam systems.

(Evaluating Method for Cross Section of Specimen)

In the following there will be explained a cross section evaluating method of the present invention.

FIG. 3 is a flow chart showing a sequence of cross sectional evaluation of a specimen with the scanning electron microscope for cross sectional observation shown in FIG. 1. In the following there will be given an explanation on the procedure of cross sectional observation, with reference to FIG. 3, together with a detailed explanation on the control for the SEM and SIM observations by control unit 7 and on the temperature control on the specimen by temperature control unit 7a with such procedure.

At first specimen 1 is fixed on a predetermined position (temperature varying mechanism 10) of specimen stage 8 (step S10) and inserted in specimen chamber 3, and an evaluation temperature is set (step S11). In response to the setting of the evaluation temperature, temperature control unit 7a controls temperature in temperature varying mechanism 10 whereby the temperature is kept at the set evaluation temperature. In this state, the temperature of specimen 1 is detected by thermometer 9a, and the operator can confirm whether specimen 1 is maintained at the evaluation temperature based on the detection temperature displayed on the unrepresented display unit.

In the present embodiment, it is preferable to effect the working in a state where the specimen is cooled from the room temperature. Also a cooling to lower than 0° C. is more preferable because the specimen can be solidified if it contains moisture.

In such a cooling process, it is preferred to cool at first the specimen to a predetermined temperature lower than the room temperature, then hold the specimen in a reduced pressure and execute a working operation by the irradiation of a focused beam while absorbing the heat generated from the vicinity of the irradiated portion of the specimen to retain the shape of the non-irradiated portion.

Also the cooling of the specimen may be achieved by rapid cooling from the room temperature. In such a case, a cooling rate of 40° C./min or higher is preferred. This method allows to observe the cross section in a rapidly cooled state in case of measuring the cross sectional state of a mixture of which dispersion state varies depending on the temperature.

The cooling step is preferably executed before the pressure reducing step, thereby allowing to suppress the evaporation of the specimen caused by the reduced pressure. However, if the specimen consists of a substance showing little evaporation, the cooling may be executed simultaneously with the pressure reduction.

The cooling depends on the specimen to be processed. In case of an ordinary organic material such as PET, it is preferably cooled to a temperature range of −0 to −200° C., preferably −50 to −150° C.

Also if the working time or the cooling time becomes excessively long at the cooling to the low temperature, a remaining gas in the specimen chamber or the substance generated at the working may be adsorbed in the specimen of low temperature, thereby eventually hindering the desired working or observation. It is therefore preferable to provide trap means for absorbing the remaining gas or the substance generated at the working operation and to execute the working or the acquisition of information while cooling such trap means.

The method of the present invention is advantageously applicable in case the object specimen is an organic material, particularly a material susceptible to heat such as a protein or other biological substances, or a moisture-containing composition. It is particularly preferable for a composition containing moisture, since the working can be executed while the moisture is retained in the specimen.

In particular, the irradiation with the focused ion beam is executed under a reduced pressure. Therefore, in case of working on a composition containing moisture or organic molecules of high volatility, there may result evaporation of moisture or such molecules by the heat generated in the course of the working operation, and the presence of the temperature regulating means of the present invention is highly effective.

It is also preferable, in order to achieve more exact working and structural evaluation, to provide a step of determining in advance an appropriate holding temperature at the working. Such preferred holding temperature can be determined by employing a specimen, equivalent to the specimen to be worked, as a reference, executing the working operation at plural temperatures and investigating the relationship between the damage in the worked portion and the cooling temperature.

In an ordinary FIB working apparatus, it has been customary to move the specimen, after the working thereof, to an SEM or another apparatus for executing operation etc., but the move to the observation means in the temperature controlled state has been difficult. The present embodiment provides a working apparatus capable of working and observation on the specimen in a cooled state, without influence on the worked surface, for example, by the deposition of water drops on the specimen at the cooling.

After the confirmation that specimen 1 is maintained at the evaluation temperature there is executed SEM observation of the surface of specimen 1, under constant confirmation of the temperature thereof (step S12). In the SEM observation, control unit 7 controls the electron beam irradiation by electron beam generation unit 5 and the movement of specimen stage 8; whereby specimen 1 is scanned by the electron beam from electron beam generation unit 5. In synchronization with the scanning operation, electron detector 6 detects the secondary electrons, and control unit 7 displays an SEM image, based on the detection signal of the secondary electrons, on the unrepresented display unit. Thus, the operator can execute SEM observation of the surface of specimen 1.

Subsequently, based on the image obtained by the SEM observation of the surface of specimen 1 (SEM image displayed on the display unit), the cross section position to be evaluated is precisely determined (step S13), and thus determined cross section position to be evaluated is further subjected to an SIM observation (step S14). In the SIM observation, control unit 7 controls the ion beam irradiation by ion beam generation unit 4 and the movement of specimen stage 8, whereby specimen 1 is scanned in the range of the cross section position to be evaluated by the ion beam from ion beam generation unit 4. In synchronization with the scanning operation, electron detector 6 detects the secondary electrons, and control unit 7 displays an SIM image, based on the detection signal of the secondary electrons, on the unrepresented display unit. Thus, the operator can execute SIM observation of the surface of specimen 1 at the cross section position to be evaluated determined in the step S14.

Then there are set FIB working conditions (step S15). In this setting of the FIB working conditions, a cut-out area and a cut-out position are determined on the SIM image obtained by the SIM observation of the surface in the step 14, and there are set the cross section working conditions including an acceleration voltage, a beam current and a beam diameter. The cross section working conditions include crude working conditions and finish working conditions, which are both set at this point. In the crude working conditions, the beam diameter and the working energy are larger than those in the finish working conditions. The cut-out area and the cut-out position can be determined on the SEM image obtained in the foregoing step S14, but, in consideration of the precision, they are preferably determined on the SIM image obtained with the ion beam which is used in the actual working.

After the setting of the FIB working conditions, there is executed an FIB working (crude working) (step S16). In the crude working, control unit 7 controls the ion beam generation unit 7 according to the crude working conditions set as explained in the foregoing, and also controls the movement of specimen stage 8 whereby the cut-out area and cut-out position determined in the step S15 is irradiated with the ion beam of an amount necessary for cutting.

After the crude working, the surface of specimen 1 is subjected to an SIM observation to confirm, on an image obtained by such SIM observation (SIM image), whether the working has proceeded close to the desired position (step S17). Also the cross section prepared by the crude working is subjected to an SEM observation to confirm the state (coarseness) of the cross section (step S18). In case the working has not proceeded close to the desired position, the aforementioned steps S16 and S17 are repeated. The steps S16 and S17 are repeated also in case the worked cross section is extremely coarse, but, in such case, there is added, for example, an operation of gradually reducing the amount of ion beam. The SIM observation of the surface in the step S17 is similarly controlled as in the foregoing step S12. Also the SEM observation of the cross section in the step S18 is controlled basically similar to the aforementioned step S12, except that specimen stage 8 is so moved that the worked cross section is irradiated by the electron beam. In this operation, the electron beam may have any incident angle to the cross section as long as an SEM image can be obtained.

After the confirmation that the crude working has proceeded close to the desired position, there is executed an FIB working (finish working) (step S19). In the finish working, control unit 7 controls the ion beam generation unit 7 according to the finish working conditions set as explained in the foregoing, and also controls the movement of specimen stage 8 whereby the crude finished portion obtained in the step S16 is irradiated with the ion beam of an amount necessary for finish working. Such finish working allows to obtain a smooth cross section, for example, enabling the observation with a high magnification with the scanning electron microscope.

Finally, thus prepared cross section of specimen 1 is subjected to an SEM observation (step S20). The control in such cross sectional SEM observation is same as that in the foregoing step S18.

As explained in the foregoing, the scanning electron microscope for cross sectional observation of the present embodiment is capable of maintaining the evaluated specimen 1 always at the set temperature, so that the state and morphology of specimen 1 do not change in the course of the FIB working. Consequently the fine structural analysis can be achieved in precise manner.

Also, the temperature of the specimen, selected in the working operation with the ion beam is preferably same as that selected at the observing operation, but the temperature in the working operation may be selected lower than that in the observing operation. In such case, there may be a temperature difference of 10 to 50° C. between the working process and the observation process.

Embodiment 2

Figure 4:
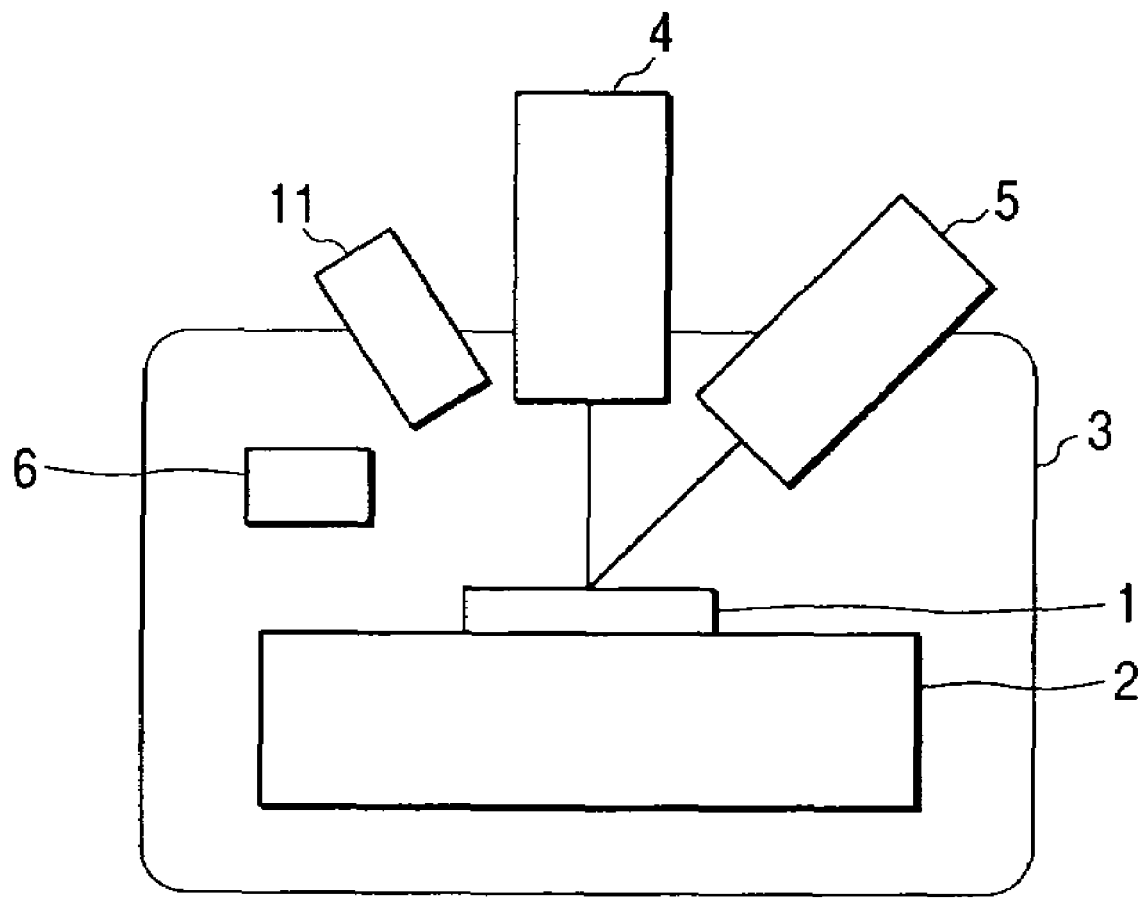
FIG. 4 is a view schematically showing the configuration of a scanning electron microscope for cross sectional observation, constituting a second embodiment of the cross section evaluating apparatus of the present invention.

FIG. 4 schematically shows the configuration of a scanning electron microscope for cross sectional observation, constituting a second embodiment of the cross section evaluating apparatus of the present invention. This electron microscope is substantially same in configuration as that of the first embodiment, except for the presence of an X-ray detector 11 for detecting characteristic X-rays emitted from specimen 1 in response to the electron beam irradiation. In FIG. 4, components equivalent to those shown in the foregoing are represented by like numbers.

Control unit 7 receives a detection signal from the X-ray detector 11, and, by scanning specimen 1 with the electron beam from electron beam generation unit 5, can execute an elementary analysis in the scanned range. Thus, the present embodiment is capable of an elementary analysis, in addition to the SEM observation and the SIM observation.

The electron microscope of the present embodiment is capable, in addition to the cross sectional evaluation of the specimen by the procedure shown in FIG. 3, of a cross sectional evaluation by the elementary analysis utilizing the aforementioned X-ray detector 11. More specifically, the elementary analysis utilizing the X-ray detector 11 is executed instead of the cross sectional SEM observation (or parallel thereto) in the step S20 in the evaluation procedure shown in FIG. 3. In the elementary analysis, control unit 7 controls the movement of specimen stage 8 in such a manner that the prepared cross section is irradiated by the electron beam from electron beam generation unit 5, and scans the cross section with the electron beam. In synchronization with the scanning operation, the X-ray detector 11 detects the characteristic X-rays from plural measuring points, and control unit 7 displays mapping information, based on the detection signal of thereof, on the unrepresented display unit. Otherwise, after the scanning of the cross section with the electron beam, a necessary position is irradiated with the electron beam and the elementary analysis is executed by detecting the characteristic X-rays generated from the irradiated position.

In order to improve the precision of the elementary analysis utilizing the aforementioned X-ray detector 11, a specimen stage with a temperature controller as shown in FIG. 5 may be employed as temperature holding unit 2. This specimen stage with temperature controller is same in configuration as that shown in FIG. 2, except for the position of temperature varying mechanism 10 and the fixing position for specimen 1. In the configuration shown in FIG. 5, temperature varying mechanism 10 is so provided that a lateral face 10a thereof is positioned at an edge portion 8a of specimen stage 8, whereby the working of cross section can be directly executed on a lateral face 1a of specimen 1 fixed on temperature varying mechanism 10.

Thus, by employing such specimen stage with temperature controller as explained above, it is rendered possible to irradiate a right-hand portion (lateral face 1a) of specimen 1 with the ion beam thereby forming a cross section in this portion. Such formation of the cross section at the side of the lateral face la of specimen 1 allows to position the cross section closer to the X-ray detector 11, and the precision of the elementary analysis can be improved by such positioning of the cross section closer to the X-ray detector 11. Also by inclining the specimen stage toward the detector, it is possible to improve the detection efficiency of the generated characteristic X-rays, and to further improve the precision of the elementary analysis.

Also such working of the cross section allows to position the cross section closer to electron beam generation unit 5 whereby the precision of the SEM image obtained with electron detector 6 can also be improved.

In the embodiments explained in the foregoing, the working of the specimen with the ion beam does not involve generation of a shear stress, a compression stress or a tensile stress as encountered in the mechanical working method such as cutting or grinding, so that a sharp cross section can be prepared even in a composite specimen consisting of a mixture of materials different in hardness or brittleness, a specimen including voids, a fine structure of organic materials formed on a substrate, a specimen easily soluble in a solvent etc.

Also, since the specimen can be maintained at the set temperature, it is possible to directly observe the designated position without destructing the layer structure, even in a specimen including a material which changes the state or shape by the. temperature.

The cross section evaluating method in the foregoing embodiments is effective for analyzing, at a desired temperature, a polymer structure on various substrates such as glass, a polymer structure containing micro particles or liquid crystals, a structure of particle dispersion in a fibrous material, or a specimen containing a material showing a temperature-dependent transition. It is naturally effective also for a material which is easily damaged by an ion beam or an electron beam.

The foregoing embodiments have been explained by an apparatus for executing the SEM observation, SIM observation and elementary analysis, but the present invention is not limited to such embodiments and is applicable also to an apparatus for executing various analyses such as mass analysis.

Further, the specimen stage with temperature controller shown in FIG. 5 can also be used as temperature holding unit 2 of the scanning electron microscope for cross sectional observation shown in FIG. 1.

Embodiment 3

Figure 6:
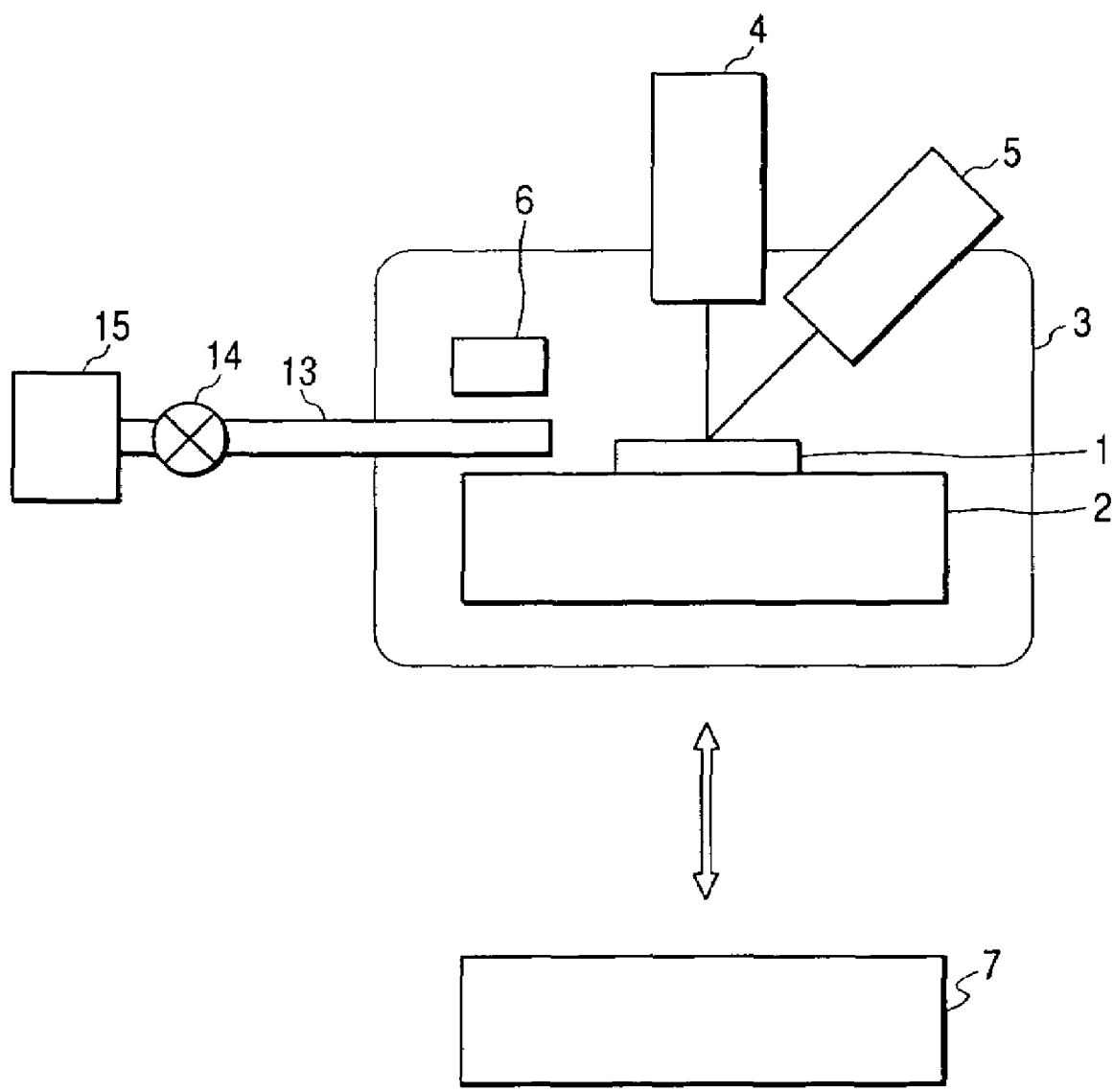
FIG. 6 is a view schematically showing the configuration of a scanning electron microscope for cross sectional observation, constituting a third embodiment of the cross section evaluating apparatus of the present invention.

In addition to the configurations of the foregoing embodiments 1 and 2, there may be provided a reactive gas introducing pipe 13 as shown in FIG. 6, in the vicinity of the specimen stage, thereby introducing a reactive gas to the vicinity of the specimen in the course of the FIB working. There are also shown a valve 14 and a gas source container 15.

In such case, there can be executed ion beam-assisted gas etching or gas deposition depending on the selected conditions of ion beam, gas and temperature, thereby working the surface of the specimen into an arbitrary shape. The observation (SEM observation or SIM observation) of thus worked surface allows to obtain exact information on the surface thus worked into the desired shape.

The gas introducing aperture is so three-dimensionally positioned as not to obstruct the detector or the beam system.

A well-known example of FIB-assisted deposition is tungsten deposition utilizing hexacarbonyl tungsten ($W(CO)_6$) and Ga-FIB.

Also it is possible to blow an organometallic gas around the FIB irradiating point, thereby causing a reaction between the FIB and the gas to deposit the metal of the gas onto the substrate.

A conventional FIB-assisted deposition apparatus without the cooling mechanism has been associated with a drawback that the underlying material is removed by the FIB before the FIB-assisted deposition is started. Therefore, the present invention is advantageous as a method of forming a desired inorganic material.

It is also possible blow an etching gas around the FIB irradiating point, thereby inducing a reactive etching locally in the beam irradiating position, and enabling a micro working of a high speed and a high selectivity.

The aforementioned FIB-assisted etching and FIB-assisted deposition can be executed under the conditions as described in Japanese Patent Application Laid-Open No. H07-312196.

Embodiment 4

As shown in FIG. 7, the present embodiment is provided, in addition to the configuration of the embodiment 1, with trap means 16 for preventing re-deposition of the gas remaining in the specimen chamber or the substances generated at the working operation, onto the specimen. Such trap means is composed for example of a material of high thermal conductivity such as a metal, and is maintained at a temperature equal to or lower than that of the specimen while it is cooled.

The present embodiment is effective, in case of working or observation in a state of maintaining the specimen lower than the room temperature, in preventing the deposition of impurities onto the specimen. For example, in the aforementioned FIB-assisted deposition, there may be formed an impurity layer between the deposition layer and the worked specimen, thereby hindering to achieve the desired function.

Such trap means is provided, in a state where the stage with the specimen supported thereon, the ion beam generation means, the electron beam generation means and the detection means are positioned, in such a position as not to hinder the beam systems in the detecting or working operation. For improving the trapping efficiency, such trap means is preferably positioned as close as possible to the specimen, as long as it does not hinder such detecting or working operation. Also the trap means may be provided in more than one unit in the specimen chamber maintained at a low pressure.

Embodiment 5

The present embodiment shows an example of applying the apparatus of the present invention as a cross section evaluating apparatus in a manufacturing process for a liquid crystal display device or an organic semiconductor device.

In the present embodiment, there will be explained a case of executing temperature regulation on the specimen of a relatively large area.

In case of exactly evaluating the cross sectional state in a part of a large-sized specimen, such as a glass- substrate coated with liquid crystal and to be used in a large-size liquid crystal display device, it is preferable to regulate the temperature of the entire substrate, though a local temperature regulation of an area around the worked portion is also possible. In such case, the entire holder may be cooled by providing a coolant pipe for circulating a cooling medium, in a position opposed to the specimen supporting surface of the temperature holding unit.

Embodiment 6

FIG. 10 is a schematic block diagram of a focused ion beam apparatus for cross section working, which is a sixth embodiment of the cross section working apparatus of the present invention. The focused ion beam apparatus comprises a temperature holding unit 2a for maintaining the temperature of a fixed specimen 1 which is fixed at a set temperature, and a holding unit 2 supporting the temperature holding unit 2a. This temperature holding unit 2a can be accommodated in the interior of a specimen chamber 3.

In the specimen chamber 3, there are provided an ion beam generation unit 4 for irradiating an ion beam to the specimen 1 fixed on the temperature holding unit 2a, and a detector 5 for detecting a signal generated from the specimen 1 irradiated with the ion beam, and also there are provided a gas introducing unit 6 and a cover 7. The interior of the specimen chamber 3 is evacuated by an unrepresented pump, and is capable of maintaining a predetermined low pressure, thereby the irradiation of the ion beam is rendered possible. In the present embodiment, the interior of the specimen chamber is preferably maintained below a pressure of $1 \times 10^2$ Pa.

The ion beam generation unit 4 can be used for S11 observation as well as for irradiating the ion beam on the specimen 1 and cutting out a cross section. In case of SIM observation, secondary electrons or secondary ions generated when the specimen 1 is irradiated with the ion beam are detected by the detector 5, and an image is formed based on the detection signal from the detector 5.

A gas introducing unit 6 is used for controlling the atmosphere around the specimen 1. Further it can also be used for increasing the pressure in the interior of the specimen chamber 3. After cutting off the specimen chamber side and a vacuum line while maintaining the ion bean generation unit 4 and the detector 5 at high vacuum by a shutter (not shown), the cover 7 in the interior of the specimen chamber 3 can be put on the specimen 1 for every temperature holding unit 2a, making the specimen chamber 3 leak. The specimen 1 is in the interior of the cover 7, and since the control of the atmosphere around the specimen is executed from the gas introducing unit 6, it is possible to select those matching the necessary conditions by the temperature and the material of the specimen 1. Further, it is also possible to execute the leaking of the specimen chamber 3 through a leaking valve (not shown).

The detection signal from the detector 5 is supplied to the control unit 9, and the control unit 9 executes the image formation at the time of the above-mentioned SIM and SEM observations. For example, the control unit 9 acquires image information (mapping information) from the detection signal from the detector 5, and forms an image by causing an unrepresented display apparatus to display such image information. In addition, the control unit 9 controls the ion beam generation in the ion beam generation unit 4, and controls the irradiation and scanning of the ion beam onto the specimen 1. The beam scanning can be controlled in the beam side or in the stage side where the specimen is fixed or in both sides, but the control at the beam side is preferable in consideration of the scanning speed and the like.

The ion beam generation unit and the like may be so constructed as disclosed in Japanese Patent Application Laid-Open No. H6-342638.

(Configuration of Temperature Regulation Means)

The temperature regulation means in the present embodiment can adopt the means described earlier in the first embodiment by using FIG. 2.

(Cross Section Evaluating Method of Specimen)

The cross section evaluating method according to the present invention will be described below. Here, what is meant by the cross section of the specimen is a cross section of an element and a material to be evaluated. Also when a specimen cross section is placed on the upper surface of the specimen in advance, it is possible to evaluate also on the information in a surface direction of a certain depth of the element and the material.

Figure 11:
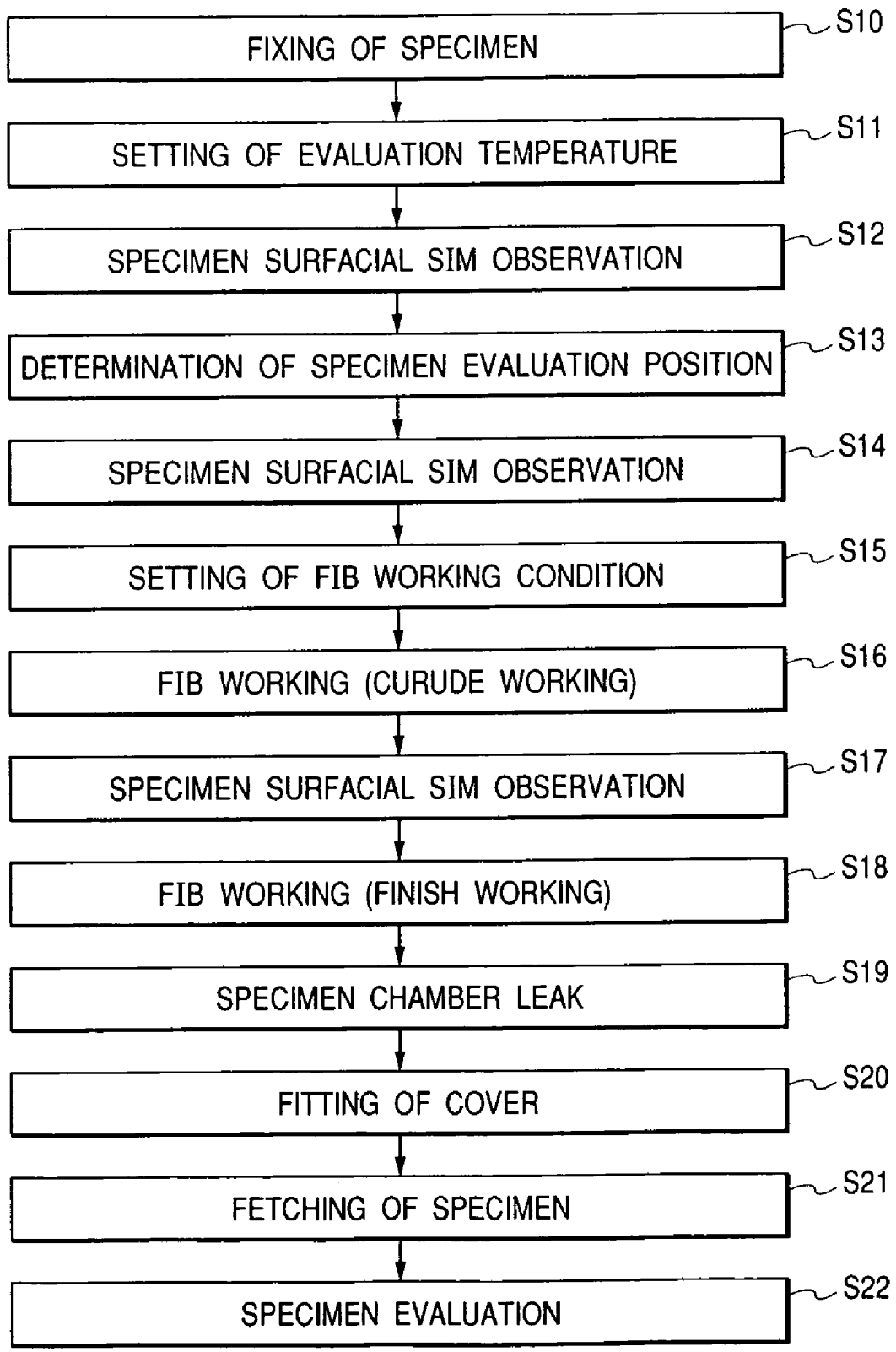
FIG. 11 is a flow chart showing a procedure of the cross section evaluation of the specimen using the focused ion beam apparatus for cross section working shown in FIG. 10.

FIG. 11 is a flowchart showing a procedure of the cross section evaluation of the specimen using the cross section working apparatus shown in FIGS. 10 and 2. The procedure of the cross section evaluation will be explained below with reference to FIG. 11, and at the same time, the control for SIM observation by the control unit 9 along this procedure and the temperature control of the specimen by a temperature control unit 7a will be also explained.

At first the specimen 1 is fixed at a predetermined position of the specimen stage 8 (position variable mechanism 12) (step S10), and after it is inserted into the specimen chamber 3, an evaluation temperature is set (step S11). When the evaluation temperature is set, the temperature in the temperature varying mechanism 10 is controlled by the temperature control unit 7a, whereby the temperature of the specimen 1 is kept at the set evaluation temperature.

The temperature of the specimen 1 at this time is detected by a thermometer 9a, and the operator can confirm whether the specimen 1 is maintained at the evaluation temperature from the detection temperature displayed at the unrepresented display unit.

In the present embodiment, it is preferable to effect the working in a state where the specimen is cooled from the room temperature. Also a cooling to below 0° C. is more preferable because the specimen can be solidified if it contains moisture.

In such a cooling process, it is preferred to cool at first the specimen to a predetermined temperature below the room temperature, then hold the specimen in a reduced pressure and execute a working operation by the irradiation of a focused beam while absorbing the heat generated from the vicinity of the irradiated portion of the specimen to retain the shape of the non-irradiated portion.

Also the cooling of the specimen may be achieved by rapid cooling from the room temperature. In such a case, a cooling rate of 40° C./min or higher is preferred. This method allows to observe the cross section in a rapidly cooled state in case of measuring the cross sectional state of a mixture of which dispersion state varies depending on the temperature.

The cooling step is preferably executed before the pressure reducing step, thereby allowing to suppress the evaporation of the specimen caused by the reduced pressure. However, if the specimen consists of a substance showing little evaporation, the cooling may be executed simultaneously with the pressure reduction.

The cooling depends on the specimen to be worked. In case of an ordinary organic material such as PET, it is preferably cooled to a temperature between 0 to −200° C., preferably −50 to −100° C.

Also if the working time or the cooling time becomes excessively long at the cooling in a low temperature, a remaining gas in the specimen chamber or the substance generated at the working may be adsorbed in the specimen of low temperature, thereby eventually hindering the desired working or observation. It is therefore preferable to provide trap means for adsorbing the remaining gas or the substance generated at the working operation and to execute the working and the acquisition of information while cooling such trap means.

The method of the present invention is advantageously applicable in case of the object specimen is an organic material, particularly a material susceptible to heat such as a protein or other biological substances, since the working can be executed while the moisture is retained in the specimen.

In particular, the irradiation with the focused ion beam is executed under a reduced pressure. Therefore, in case of working on a composition containing moisture or organic molecules of high volatility, there may result evaporation of moisture by the heat generated in the course of the working operation, and the presence of the temperature regulation means of the present invention is highly effective.

It is also preferable, in order to achieve more exact working and structural evaluation, to provide a step of determining in advance an appropriate holding temperature at the working. Such preferred holding temperature can be determined by employing a specimen, equivalent to the specimen to be worked, as a reference, executing the working operation at plural temperatures and investigating the relationship between the damage in the worked portion and the cooling temperature.

Also in an ordinary FIB working apparatus, it has been customary to move the specimen, after the working thereof, to an SEM or another apparatus for executing operation and the like, but in this case, since the specimen is exposed to the atmosphere, it has been necessary to restore the temperature of the specimen once to the ordinary temperature, and then to move the specimen to the observation means. The present embodiment can execute the observation after the specimen is worked in a cooled state, and can provide an adequate working of the specimen without a possibility of affecting the working surface by allowing moisture to adhere on the surface of the specimen to be cooled.

After the confirmation that specimen 1 is maintained at the evaluation temperature, there is execute SIM observation of the surface of specimen 1, under constant confirmation of the temperature thereof (step S12). In the SIM observation, control unit 9 controls the electron beam irradiation by electron beam generation unit 4 and the movement of specimen stage 8, whereby specimen 1 is scanned by the ion beam from ion bean generating unit 4. In synchronization with the scanning operation, the detector 5 detects the secondary electrons (or secondary ion: hereinafter, it is the same), and the control unit 9 displays an SIM image, based on the detection signal of the secondary electrons, on the unrepresented display unit. Thus, the operator can execute SIM observation of the surface of specimen 1. The SIM observation is executed by using a weak ion beam for the observation. This SIM observation uses a weak ion beam for observation.

Subsequently, based on the image obtained by the SIM observation (SIM image displayed on the display unit), the cross section position to be evaluated is precisely determined (step S13), and thus determined cross section position to be evaluated is further subjected to an SIM observation by the working beam (step S14).

Then there are set FIB working conditions (step S15). In this setting of the FIB working conditions, a cut-out area and a cut-out position are determined on the SIM image obtained by the SIM observation of the surface in the step S14, and there are set the cross section working conditions including an acceleration voltage a beam current and a beam diameter. The cross section working conditions include crude working conditions and finish working conditions, which are both set at this point. In the crude working conditions, the beam diameter and the working energy are larger than those in the finish working conditions. The cut-out area and the cut-out position can be determined on the SIM image with the observation beam obtained in the foregoing step S12, but, in consideration of the precision, they are preferably determined on the SIM image obtained with the ion beam which is used in the actual working.

After the setting of the FIB working conditions, there is first executed an FIB working (crude working) (step S16). In the crude working, control unit 9 controls the ion beam generation unit 4 according to the crude working conditions set as explained in the foregoing, and also controls the movement of specimen stage 8 whereby the cut-out area and cut-out position determined in the step S15 are irradiated with the ion beam of an amount necessary for cutting.

After the crude working, the surface of specimen 1 is subjected to an SIM observation to confirm, on an image obtained by such SIM observation (SIM image), whether the working has proceeded close to the desired position (step S17). In case the working has not proceeded close to the desired position, the aforementioned steps S16 and S17 are repeated. The steps S16 and S17 are repeated also in case the SIM image of the worked cross section surface is extremely coarse, but, in such case, there is added, for example, an operation of gradually reducing the amount of ion beam. The SIM observation of the surface in the step S17 is similarly controlled as in the foregoing step S12.

After the confirmation that the crude working has proceeded close to the desired position, there is executed an FIB working (finish working) (step S18). In the finish working, control unit 9 controls the ion beam generation unit 4 according to the finish working conditions set as explained in the foregoing, and also controls the movement of specimen stage 8 whereby the crude finished portion obtained in the step S16 is irradiated with the ion beam of an amount necessary for finish working. Such finish working allows to obtain a smooth cross section, for example, enabling the observation with high magnification with the scanning electron microscope.

Next, after the specimen chamber side and the vacuum line are cut off by an unrepresented shutter while maintaining the ion beam generation unit 4 and the detector 5 at high vacuum, the specimen chamber 3 is leaked (step S19). Though the gas used for the leaking at this time is adequately selectable depending oh the evaluation specimen material and the evaluation temperature, it is preferable to use a dry gas eliminated from moisture and the like in order to prevent moisture and the like from adhering on the specimen. For example, a nitrogen, an inactive gas and the like are used. Also as occasion demands, a gas of a set temperature is used so as to minimize the temperature change in the specimen.

Also the cover 7 in the interior of the specimen chamber 3 is put on specimen 1 for every temperature holding unit 2*a* (step S20), and while the atmosphere in the interior of the cover is controlled by gas introducing unit 6, the specimen stage having specimen 1, with the cover 7 fitted as it is, is fetched from the specimen chamber (step S21).

Finally, thus prepared and fetched specimen 1 is moved to another evaluation apparatus (for example, SEM), and the evaluation of the specimen cross section is executed (step S22).

As explained in the foregoing, the cross sectional observation method is capable of maintaining the evaluated specimen 1 always at the set temperature, so that the state and morphology of specimen 1 do not change in the course of the FIB working.

In the embodiment as explained in the foregoing, since the working of specimen by ion beam does not cause a shear stress, a compression stress, and a tensile stress, it is possible to prepare a sharp cross section in a composite material mixed with materials different in hardness and brittleness, a specimen including a void, a fine structure of organic materials formed on a substrate, and a specimen easily soluble in a solvent and the like.

Also since the specimen temperature can be maintained at a set value, even if the specimen is such as including the material of which state and shape change by the temperature, a designated position can be directly observed without destructing the layer structure.

The cross sectional evaluation method in each of the morphology explained in the foregoing is effective for analyzing, at a desired temperature, polymer structures of various bases such as glass, a polymer structure containing micro particles or liquid crystals, a structure of particle dispersion in a fibrous material or a specimen containing a material showing a temperature-dependent transition. It is naturally effective also for a material which is easily damaged by an ion beam or an electron beam.

Figure 12:
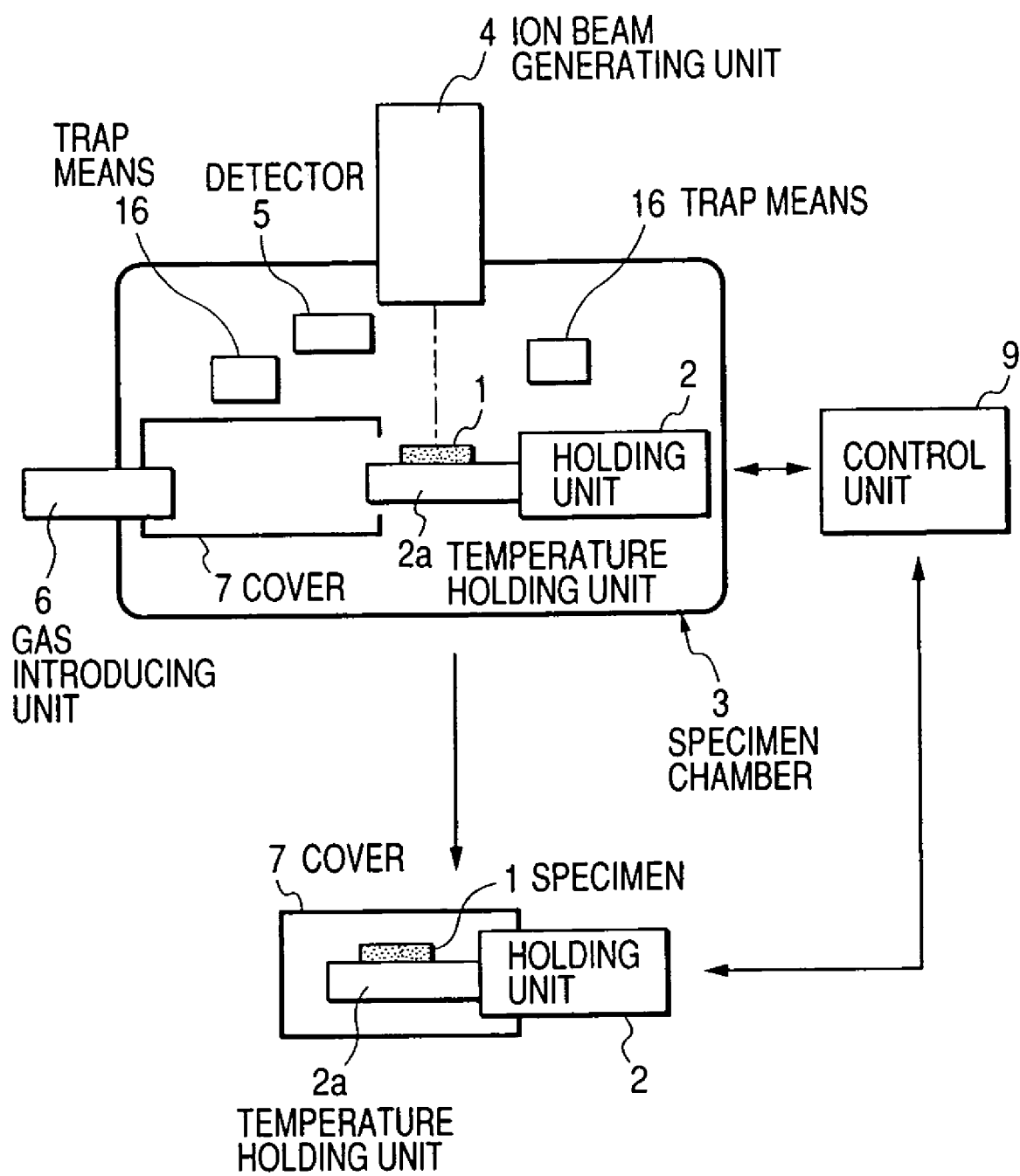
FIG. 12 is a schematic block diagram of the focused ion beam apparatus for cross section working, which is a seventh embodiment of the cross section evaluation apparatus of the present invention.

In addition to the working apparatus shown in FIG. 10, the apparatus shown in FIG. 12 is an apparatus added with trap means 16 on the apparatus shown in FIG. 10. The operation and the like of the trap means 16 are explained in the fourth embodiment.

Embodiment 7

Figure 13:
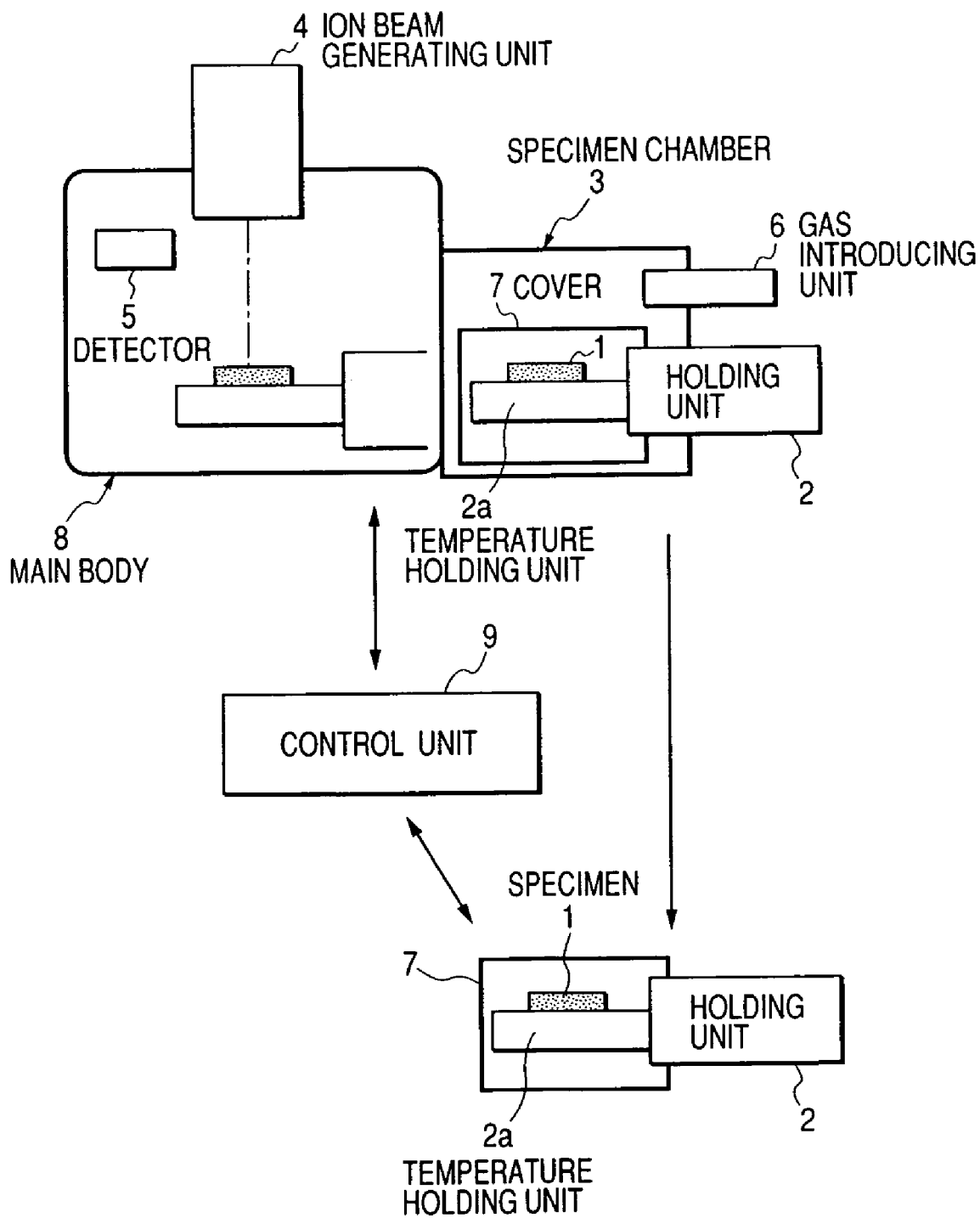
FIG. 13 is a schematic block diagram of the scanning electron microscope for observing worked cross section, which is an eighth embodiment of the cross section evaluation apparatus of the present invention.

In the present embodiment, as shown in FIG. 13, an apparatus having a configuration cut off from a main body to execute a working on a specimen in a specimen chamber is shown. After the working on a specimen is executed in the interior of the main body 8, the specimen is moved to a specimen chamber with a vacuum maintained, and after the main body 8 is cut off from a vacuum line, a dry gas can be introduced from a gas introducing unit 6, similarly to the first embodiment, whereby not only the gas introduction is not extended at all to the whole of the main body 8, but also the configuration is made such that the size of the specimen chamber 3 can be minimized. Hence, the amount of gas from the gas introducing unit can be reduced, so that the temperature of specimen 1 can be easily controlled.

EXAMPLES

In the following there will be explained examples of cross sectional evaluation with the cross section evaluating apparatus of the foregoing embodiments.

Example 1

The present example employed the scanning electron microscope for cross sectional observation shown in FIG. 1. Temperature holding unit 2 consisted of a unit of the specimen stage with temperature controller as shown in FIG. 2, coupled with a low-temperature varying mechanism, and there was executed a cross sectional evaluation of a specimen, prepared by forming a polymer structure containing liquid crystal (two-frequency drive liquid crystal DF01XX, manufactured by Chisso Co.) (structure being obtained by mixing and polymerizing synthesized monomers HEMA, R167 and HDDA with liquid crystal) on a glass substrate, in the following procedure.

At first the specimen was fixed with carbon paste on the unit provided with the low-temperature varying mechanism, and this unit was set on specimen stage 8. After specimen stage 8 with the specimen set thereof was introduced in specimen chamber 3, the interior thereof was evacuated to a predetermined low pressure.

Then the temperature was set at −100° C., and it was confirmed that the specimen was maintained at such evaluation temperature. Under constant confirmation of the temperature of the specimen, there was executed surficial SEM observation of an area of the specimen including the cross section observing position. Based on the image obtained by the surficial SEM observation, an approximately central portion of the specimen was determined as the cross section observing position.

Then the determined cross section observing position was irradiated with the ion beam to obtain an SIM image. The ion beam used in this operation was made very weak, in the observation mode. More specifically, there was employed a gallium ion source, with an acceleration voltage of 30 kV, a beam current of 20 pA and a beam diameter of about 30 nm. A cross section working portion was designated on the obtained SIM image.

Then the designated cross section working position was subjected to FIB working (crude working). More specifically, there were employed an acceleration voltage of 30 kV, a beam current of 50 nA and a beam diameter of about 300 nm to form a rectangular recess of a side of 40 m and a depth of 30 m in the cross section working position. The crude working was executed stepwise in small amounts under a weak condition, and the cross section of the specimen was often SEM observed in the course of working in order to confirm that the working proceeds close to the desired position. When the working was almost completed, the beam was switched to an electron beam and the cross section under working was so adjusted that it could be scanned by the electron beam with an angle of about 60° thereto, and an SEM observation of the cross section was executed.

Figure 8A:
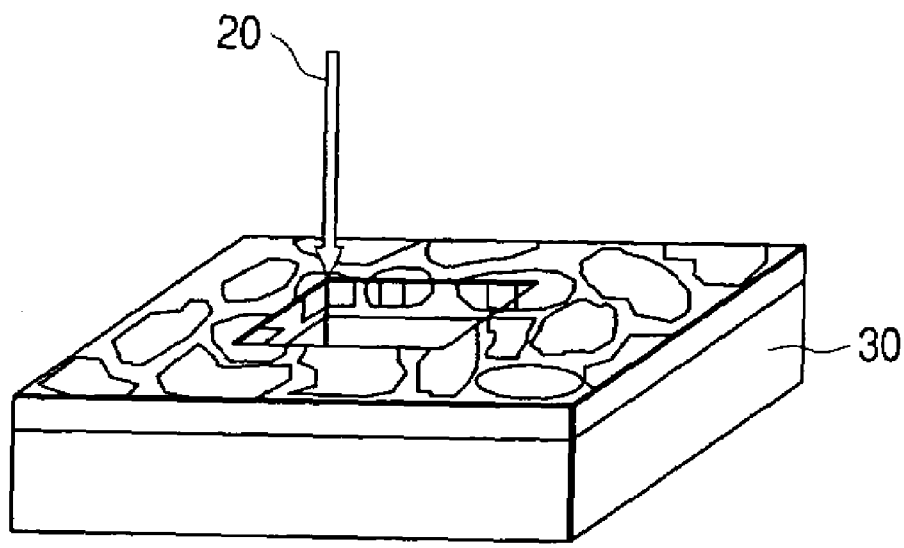

After confirmation that the working proceeded to the desired position, the beam was switched to an ion beam, and the cross section working position, obtained by crude working, was further subjected to a finish working-for improving the precision of the cross section working, under a weak condition similar to that in the SIM observation but with a finer beam than in the crude working. FIG. 8A schematically shows the cross section prepared by the above-mentioned FIB working, wherein a rectangular recess is formed by the irradiation of the ion beam 20, at the approximate center of the specimen 30.

Figure 8B:
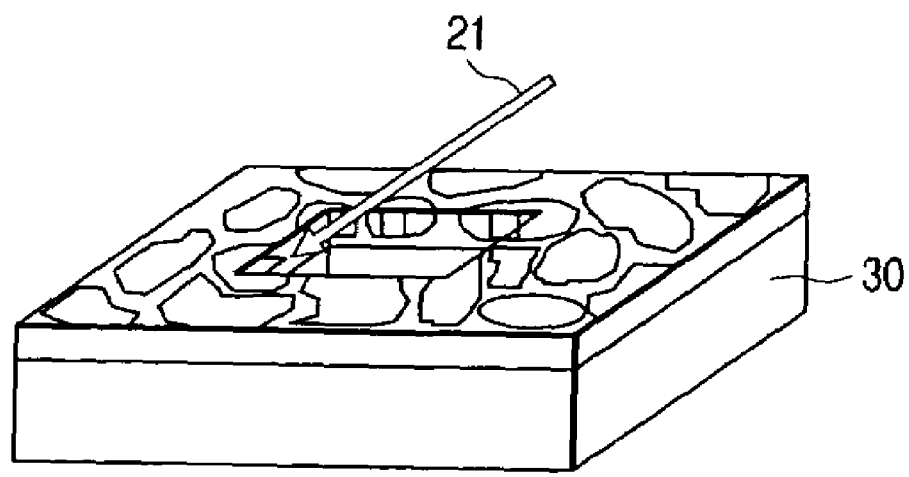
FIG. 8B is a schematic view showing a state of SEM observation of the cross section shown in FIG. 8A.

Finally, the cross section of the specimen thus prepared was subjected to an SEM observation. FIG. 8B shows the mode of electron beam irradiation at such SEM observation. The cross section of the specimen 30 shown in FIG. 8A was so adjusted as to be scanned by the electron beam 21 at an angle of about 60°, and the SEM observation was executed by scanning the cross section of the specimen 30 with the electron beam 21. The SEM observation was executed under the conditions of an acceleration voltage of 800 V and a magnification up to 50,000×, and allows to observe the state of the liquid crystal enclosed in the polymer layer.

In this example, the cross section could be worked without deformation of the liquid crystal layer in the course of working, since the FIB working was executed while the specimen was maintained at −100° C. Also the cross section showing the liquid crystal present in the polymer could be observed since the SEM observation could be executed in the same specimen chamber while a same temperature was maintained.

Example 2

The present example employed the specimen stage with temperature controller shown in FIG. 5 as temperature holding unit 2, and the cross sectional evaluation of polymer particles (polystyrene) prepared on a PET substrate, was executed in the following procedure.

Figure 9A:
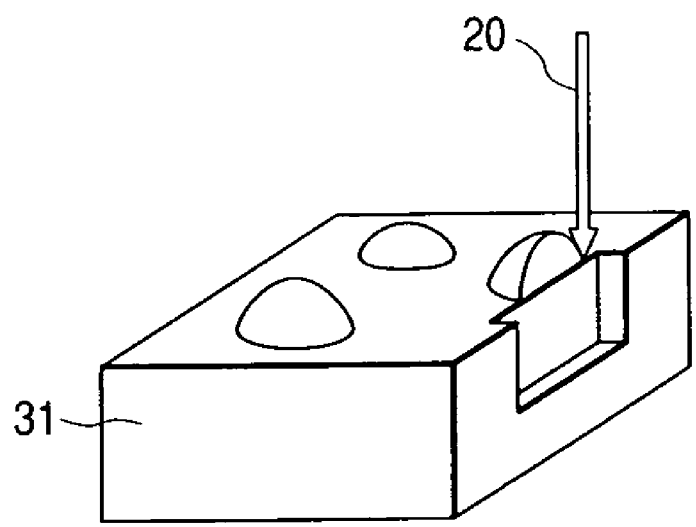

The temperature was set at about 10° C., and a side of the specimen was worked to form a notch of a length of about 20 m, a width of about 10 m and a depth of about 60 m. In order to prevent charging phenomenon, a platinum film of a thickness of about 30 nm was deposited, prior to the FIB working, by ion beam sputtering onto the surface of the specimen. Then hexacarbonyl tungsten was introduced and an FIB irradiation was executed so as to cover the polymer particles, thereby depositing a tungsten film as a protective film. Subsequently a finish working was executed under conditions similar to those in the example 1. FIG. 9A schematically shows the cross section prepared by the FIB working, wherein a rectangular recess is formed by the irradiation of the ion beam 20, on a lateral face (corresponding to the lateral face la in FIG. 5) of the specimen 31.

Then an SEM of the specimen 31 in an inclined state proved that the polymer particles were closely adhered to the substrate. The SEM observation were executed under conditions of an acceleration voltage of 15 kV and a magnification up to 30,000×.

Figure 9B:
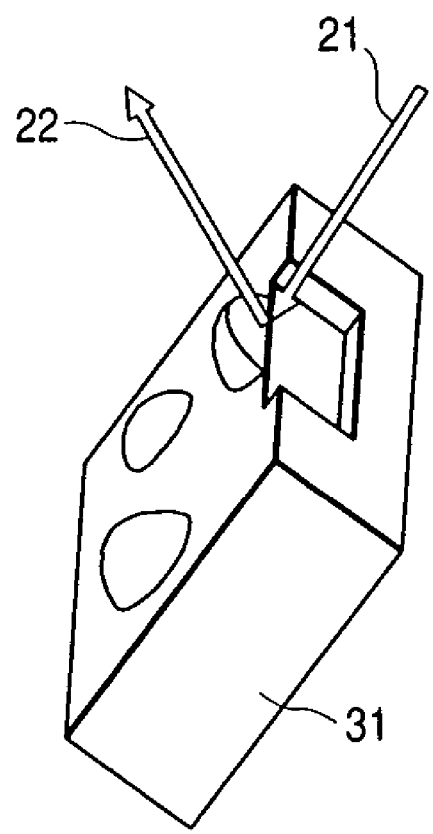
FIG. 9B is a schematic view showing a state of elementary analysis of the cross section shown in FIG. 9A.

Then the characteristic X-rays emitted from the cross section of the specimen 31 in the course of the above-mentioned SEM observation were fetched to obtain a mapping image (elementary analysis), which proved that aluminum was dispersed in polymer. FIG. 9B is a schematic view showing the irradiation of the electron beam and the emission of the characteristic X-rays at the elementary analysis. The electron beam 21 perpendicularly irradiates the cross section of the specimen 31 shown in FIG. 9A, and the characteristic X-rays are emitted in response from the cross section of the specimen 31. The elementary analysis was executed by detecting such characteristic X-rays.

In the foregoing, there has been explained a method of evaluating the cross section of a specimen, but the present invention is not limited to such case. The present invention also includes, for example, a configuration of eliminating substances deposited on the surface, exposing a surface to be observed and observing such surface.

Also for exposing the surface, there can be employed any means capable of exposing a surface of which information is desired, and laser beam generation means can be advantageously adopted in addition to the ion beam generation means.

Example 3

The present example employed the focused ion beam apparatus for cross section working shown in FIG. 10. Using temperature holding unit 2a comprised of a unit coupled wit a low temperature varying mechanism on a specimen stage with a temperature controller shown in FIG. 2, there was executed a cross sectional evaluation of a specimen prepared by forming a polymer structure containing liquid crystal (two-frequency drive liquid crystal DF01XX, manufactured by Chisso Co.) (structure being obtained by mixing synthesized monomers HEMA, R167 and HDDA with liquid crystal and polymerizing them) on a glass structure, in the following procedure.

At first the specimen was fixed with carbon paste on the unit provided with the low-temperature varying mechanism, and this unit was set on specimen stage 8. After specimen stage 8 with the specimen set thereof was introduced in specimen chamber 3, the interior thereof was evacuated to a predetermined low pressure.

Then the temperature was set at −100° C., and it was confirmed that the specimen was maintained at such evaluation temperature. Under constant confirmation of the temperature of the specimen, there was executed surfacial SIM observation of an area of the specimen including the cross section observing position. The ion beam used in this operation was made very weak, in the observation mode. More particularly, there was employed a gallium ion source, with an acceleration voltage of 30 kV, a beam current of 20 pA and beam diameter of about 30 nm. A cross section working portion was determined on the obtained SIM mode.

Then the determined cross section working position was subjected to FIB working (crude working). More specifically, there were employed an acceleration voltage of 30 kV, a beam current of 50 nA and a beam diameter of about 300 nm to form a rectangular recess of a side of 40 m and a depth of 30 m in the cross section working position. The crude working was executed stepwise in small amounts under a weak condition, and the cross section of the specimen was often SIM observed in the course of working, in order to confirm that the working proceeds close to the desired position. When the working was almost completed, the beam was switched to an electron beam and the cross section under working was so adjusted that it could be scanned by the electron beam with an angle of about 60° thereto, and an SIM observation of the cross section was executed.

After confirmation that the working proceeded to the desired position, the cross section working position, obtained by a beam finer than that in crude working, was further subjected to a finish working, under a weak condition similar to that in the SIM observation. FIG. 8A schematically shows the cross section prepared by the above-mentioned FIB working, wherein a rectangular recess is formed by the irradiation of the ion beam 20, at the approximate center of the specimen 30. This was confirmed, in the course of the cross sectional SIM observation, by including the stage and irradiating an observational weak ion beam with an angle as shown in FIG. 8B.

Then the pressure of specimen chamber 3 was slightly increased by dry nitrogen eliminated from moisture, and after that, the cover 7 was put on the specimen while the similar dry nitrogen was introduced from the cover 7 from the gas introducing unit 6, and then, specimen 1 was fetched from the FIB apparatus.

Finally, the specimen thus prepared was introduced to SEM while maintaining the specimen temperature, and the cross section thereof was subjected to the SEM observation.

The SEM observation was executed under the conditions of an acceleration voltage of 800 V and a magnification up to 50,000×, and allows to observe the state of the liquid crystal enclosed in the polymer layer.

In this example as explained in the foregoing, the cross section could be worked without deformation of the liquid crystal layer in the course of working, since the FIB working was executed while the specimen was maintained at −100° C. Also the cross section showing the liquid crystal present in the polymer could be observed since the cross section was introduced to SEM and the SEM observation could be executed in the same specimen chamber while the same temperature was maintained.

Example 4

The present example executed the cross sectional evaluation of polymer particles (polystyrene) prepared on a PET substrate in the following procedure. The working portion was the end portion of the specimen, and the evaluation was divided into the SEM observation and an element analysis.

The temperature was set at about 10° C., and a side of the specimen was worked to form a notch of a length of about 20 m, a width of about 10 m and a depth of about 60 m. In order to prevent charging phenomenon, a platinum film of a thickness of about 100 nm was deposited, prior to the FIB working, by ion beam sputtering onto the surface of the specimen. The other side was subjected up to the final working under the same conditions as those in the foregoing first example. FIG. 9A schematically shows the cross section prepared by the FIB working, wherein a rectangular recess is formed by the irradiation of the ion beam 20, on a lateral face of the side of the specimen 31.

Then a cover was put on similarly to the third embodiment, and a specimen was introduced to SEM fitted with an EDS detector. The specimen 31 was inclined and subjected to the SEM observation, which proved that polymer particles were adhered onto the substrate. The conditions at this time were an acceleration voltage of 15 kV and a magnification of up to 30,000×.

Then the characteristic X-rays emitted from the cross section of the specimen 31 in the course of the above-mentioned SEM observation were fetched to obtain a mapping image (elementary analysis), which proved that aluminum was dispersed in polymer. FIG. 9B is a schematic view showing the irradiation of the electron beam and the emission of the characteristic X-rays at the elementary analysis. The electron beam 21 perpendicularly irradiates the cross section of the specimen 31 shown in FIG. 9A, and the characteristic X-rays are emitted in response from the cross section of the specimen 31. The elementary analysis was executed by detecting such characteristic X-rays.

In the present example, there has been explained a method of evaluating the cross section of a specimen, but the present invention is not limited to such method. The present invention also includes, for example, a configuration of eliminating substance deposited on the surface, exposing a surface to be observed and observing such surface.

What is claimed is:

1. A method for processing a specimen with a focused ion beam, the specimen having a dispersion state which varies depending on temperature, said method comprising the steps of:
   placing the specimen on a stage;
   cutting out a part of the specimen by irradiating the specimen with a focused ion beam to carry out cross-sectional processing of the specimen; and
   cooling the specimen with a cooling rate of 40° C./min or more during the cutting-out step to retain the shape of a portion not irradiated with the focused ion beam.

2. The method for working a specimen according to claim 1, wherein the specimen is cooled in the cooling step so as not to change the state or form of the specimen with a heat generated by the irradiation with the ion beam.

* * * * *